United States Patent
Reddy et al.

(10) Patent No.: US 6,906,196 B2
(45) Date of Patent: *Jun. 14, 2005

(54) PROCESSES FOR THE PREPARATION OF 1, 5-DIARYL-3-SUBSTITUTED-PYRAZOLES

(75) Inventors: M. V. Ramana Reddy, Upper Darby, PA (US); Stanley C. Bell, Narberth, PA (US)

(73) Assignee: Onconova Therapeutics, Inc., Lawrenceville, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 10/246,565

(22) Filed: Sep. 18, 2002

(65) Prior Publication Data

US 2003/0109709 A1 Jun. 12, 2003

Related U.S. Application Data

(60) Provisional application No. 60/323,479, filed on Sep. 18, 2001.

(51) Int. Cl.[7] .............................................. C07D 231/10
(52) U.S. Cl. ............................. 548/377.1; 548/373.1; 548/375.1; 548/376.1; 549/59; 549/429; 549/475; 546/275.4
(58) Field of Search ..................... 548/375.1, 376.1, 548/377.1, 373.1; 549/59, 429, 475; 546/275.4

(56) References Cited

U.S. PATENT DOCUMENTS

| | | | |
|---|---|---|---|
| 2,974,141 A | 3/1961 | Pine | |
| 5,563,165 A | 10/1996 | Talley et al. | 514/406 |
| 5,675,017 A | 10/1997 | Hamper et al. | |
| 5,932,598 A | 8/1999 | Talley et al. | 514/341 |
| 6,060,605 A | 5/2000 | Lantzsch | |
| 6,376,519 B1 | 4/2002 | Reddy et al. | 514/341 |
| 6,391,906 B2 | 5/2002 | Gunduz et al. | |
| 6,579,988 B2 * | 6/2003 | Reddy et al. | 548/377.1 |

FOREIGN PATENT DOCUMENTS

| WO | WO 9746534 | 12/1997 |
|---|---|---|
| WO | WO 97-46534 | 12/1997 |

OTHER PUBLICATIONS

Penning, et al., Synthesis and Biological Evaluation of the 1,5–Diarylpyrazole Class of Cycloocygenase–2 Inh . . . , Journal of Medicinal Chemistry, 1997, (19pp.), vol. 40, No. 9.

International Search Report for PCT/US02/29581 (Mailing Date Mar. 3, 2003).

U.S. Appl. No. 10/245,949, filed Sep. 18, 2002, Reddy et al.

Penning, et al. 1997. J. Med. Chem. 40:1347–1365 Synthesis and Biological Evaluation of the 1,5–Diarylpyrazole Class of Cyclooxygenase–2 Inhibitors: Identification of 4–[5–(4–Methylphenyl)–3–(trifluoromethyl)–1H–pyrazol–1–yl]benzenesulfonamide (SC–58635, Celecoxib).

Talley, et al. 2000. J. Med. Chem. 43:1661–1663 "N–[[(5–Methyl–3–phenylisoxazol–4–yl)–phenyl]sulfonyl]propanamide, sodium salt, parecoxib sodium: A potent and selective inhibitor of COX–2 for parenteral administration". SciFinder Search (Jul. 22, 2003).

Li, Qing X. et al, Structure Activity Studies . . . , Biorganic & Medicinal Chemistry, 1994, 2(12), pp 1423–1424.

Shen, Yanchang et al, Studies of the Application . . . , Synthesis, 1984, 1, pp 35–37.

Kitazume Tomoya et al., A Convenient Synthesis . . . , Chemistry Letters, 1980, 10, 1327–1328.

Linderman et al., Chemical Abstracts, vol. 112, No. 72250, 1990.

* cited by examiner

*Primary Examiner*—Golam M M Shameem
(74) *Attorney, Agent, or Firm*—Fox Rothschild, LLP

(57) ABSTRACT

Provided are processes and chemical intermediates useful for preparing a compound of the formula I

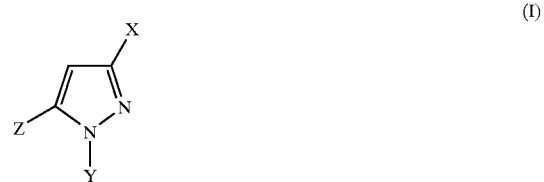

(I)

wherein

X is selected from the group consisting of $C_1$–$C_6$ trihalomethyl; $C_1$–$C_6$ alkyl; and an optionally substituted or di-substituted phenyl group of formula II:

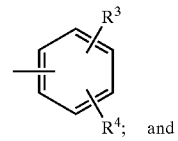

$R^4$; and

Y and Z are independently selected from the group consisting of substituted and unsubstiotuted aryl

9 Claims, No Drawings

PROCESSES FOR THE PREPARATION OF 1,5-DIARYL-3-SUBSTITUTED-PYRAZOLES

This application claims the benefit of U.S. Patent Application No. 60/323,479, filed Sep. 18, 2001, the disclosure of which is herein incorporated by reference as if fully set forth herein.

The present invention relates to processes for the preparation of 1,5-diaryl-3-substituted-pyrazoles, and chemical intermediates that serve as useful intermediates in the preparation of 1,5-diaryl-3-substituted-pyrazoles. 1,5-diaryl-3-substituted-pyrazoles are particularly useful in the treatment of inflammation and inflammation-related disorders, including arthritis.

Selective inhibitors of cyclooxygenase-2 (COX-2) have demonstrated effective anti-inflammatory activity with reduced gastrointestinal side effects, as compared to other antiinflammatory agents, e.g., NSAIDs, that inhibit both the constitutive form of cyclooxygenase (COX-1), and the inducible form of the enzyme, COX-2. A particularly effective structural class of selective COX-2 inhibitors are the 1,5-diaryl-3-substituted-pyrazoles. For example, the compound, 4-[5-(4-methylphenyl)-3-(trifluoromethyl)-1H-pyrazol-1-yl]benzenesulfonamide (celecoxib®) has been approved by the Food and Drug Administration for the treatment of rheumatoid arthritis and osteoarthritis Penning et al. (*J. Med Chem.* 1997, 40, 1347–1365) discloses that 1,5-diarylpyrazoles can be prepared by condensation of 1,3-dicarbonyl adducts with aryl hydrazines. The 1,3-dicarbonyl adducts can be prepared by Claisen condensations of aryl methyl ketones with carboxylic acid esters. In an alternate preparation, the 1,5-diaryl-3-substituted-pyrazoles can be synthesized by epoxidation of β-aryl-α,β-unsaturated ketones, followed by condensation of the resulting epoxides with arylhydrazines.

SUMMARY OF THE INVENTION

In one embodiment, the invention relates to a process for preparing a compound of the formula I

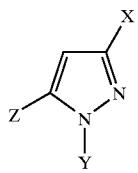

(I)

wherein X is selected from the group consisting of $C_1$–$C_6$ trihalomethyl, preferably trifluoromethyl; $C_1$–$C_6$ alkyl; and an optionally substituted or di-substituted phenyl group of formula II:

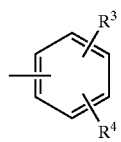

(II)

wherein $R^3$ and $R^4$ are independently selected from the group consisting of hydrogen, halogen, preferably chlorine, fluorine and bromine; hydroxyl; nitro; $C_1$–$C_6$ alkyl, preferably $C_1$–$C_3$ alkyl; $C_1$–$C_6$ alkoxy, preferably $C_1$–$C_3$ alkoxy; carboxy; $C_1$–$C_6$ trihaloalkyl, preferably trihalomethyl, most preferably trifluoromethyl; cyano; alkylsulfonyl, sulfamyl, phosphonato, and hydroxyalkyl; and Y and Z are independently selected from the group consisting of substituted and unsubstituted aryl.

The process includes the step of condensing an alkyne of formula III

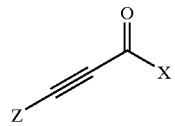

(III)

with an aryl hydrazine of the formula Y—$NHNH_2$ (IV) or a salt thereof.

In some embodiments of the process, preferred aryl groups Y and Z include phenyl and heteroaryl, which maybe substituted or unsubstituted. By "substituted" is meant any level of substitution, although mono- di- and tri-substitution are preferred. The substituents are independently selected. The substituents are preferably selected from the group consisting of halogen, particularly chlorine, fluorine and bromine; hydroxyl; nitro; $C_1$–$C_6$ alkyl, preferably $C_1$–$C_3$ alkyl, most preferably methyl, $C_1$–$C_6$ alkoxy, preferably $C_1$–$C_3$ alkoxy, most preferably methoxy; carboxy; $C_1$–$C_6$ trihaloalkyl, preferably trihalomethyl, most preferably trifluoromethyl; cyano and a group of the formula

wherein $R^5$ is $C_1$–$C_6$ alkyl or amino. Although mono-, di- and tri-substitution is preferred, full substitution, particularly when the aryl group is phenyl, is possible.

According to another embodiment of the process, Y is substituted or unsubstituted heteroaryl. Such heteroaryl radicals include, for example, pyridyl, particularly 2-, 3- and 4-pyridyl; thienyl, particularly 2- and 3-thienyl; furyl, particularly 2- and 3-furyl; indolyl, particularly 3-, 4-, 5-, 6- and 7-indolyl; benzothienyl, particularly 3-, 4-, 5-, 6-, and 7-benzothienyl; benzofuryl, particularly 3-, 4-, 5-, 6-, and 7-benzofuryl; imidazolyl, particularly 2- and 5-imidazolyl; pyrazolyl, particularly 3- and 5-pyrazolyl, 2-thiazolyl; 2-benzothiazolyl; quinolinyl, particularly 2-, 3- and 4-quinolinyl; and 4-(2-benzyloxazolyl).

In another embodiment of the process, Y is selected from the group consisting of unsubstituted phenyl, mono-, di-, and trisubstituted phenyl. Preferred radicals wherein Y is substituted phenyl include one or more of halogen, hydroxyl, nitro, $C_1$–$C_6$ alkyl, $C_1$–$C_6$ alkoxy, carboxy, $C_1$–$C_1$ trihaloalkyl, cyano, or a group of the formula

wherein $R^5$ is $C_1$–$C_6$ alkyl or amino. In a preferred embodiment, Y is a group of the formula

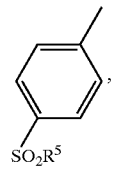

particularly where $R^5$ is amino.

According to another embodiment of the process, Z is substituted or unsubstituted heteroaryl. Such heteroaryl radicals include, for example, pyridyl, particularly 2-, 3- and 4-pyridyl; thienyl, particularly 2- and 3-thienyl; furyl, particularly 2- and 3-furyl; indolyl, particularly 3-, 4-, 5-, 6- and 7-indolyl; benzothienyl, particularly 3-, 4-, 5-, 6- and 7-benzothienyl; benzofuryl, particularly 3-, 4-, 5-, 6- and 7-benzofuryl; imidazolyl, particularly 2- and 5-imidazolyl; pyrazolyl, particularly 3- and 5-pyrazolyl; 2-thiazolyl, 2-benzothiazolyl; quinolinyl, particularly 2-, 3- and 4-quinolinyl; and 4-(2-benzyloxazolyl). In a preferred embodiment Z is 3-indolyl Representative preferred substituted heteroaryl groups include 6-methyl-2-pyridyl, 5-halo-2-thienyl, 5-methyl-2-thienyl, 5-halo-2-furyl, 5-halo-3-furyl, 2,5-dimethyl-3-thienyl and 2,5-dimethyl-3-furyl.

In another embodiment of the process, Z is selected from the group consisting of unsubstituted phenyl, mono-, di-, and trisubstituted phenyl. Preferred radicals wherein Z is substituted phenyl include, for example, one or more of halogen, hydroxyl, nitro, $C_1$–$C_6$ alkyl, $C_1$–$C_6$ alkoxy, carboxy, $C_1$–$C_6$ trihaloalkyl and cyano.

In a preferred embodiment of the process, X is trifluoromethyl; Y is 4-sulfamyl; and Z is substituted phenyl, preferably p-methyl.

In other embodiments of process, the alkyne of the formula III

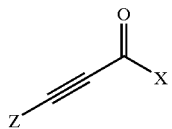

(III)

is prepared by:
(i) adding bromine to an α,β-unsaturated ketone of formula V

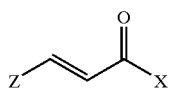

(V)

wherein X and Z are as defined above; and
(ii) contacting the product of step (i) with a base.

In embodiments of the process wherein X is trifluoromethyl, the α,β-unsaturated ketone of formula V can be prepared by treating a compound of the formula IX

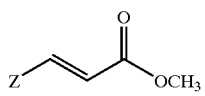

(IX)

with trimethyl(trifluoromethyl)silane in the presence of a cesium fluoride.

In an another embodiment the compound of the formula III can be prepared by condensing a methyl ketone of the formula X

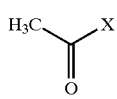

(X)

wherein X is $C_1$–$C_6$ trihalomethyl, preferably trifluoromethyl; $C_1$–$C_6$ alkyl; or an optionally substituted or di-substituted phenyl group of formula II; with an aryl aldehyde of the formula XII

Z—CHO            (XII).

In another embodiment, the compound of the formula III can be prepared by contacting an aryl acetylene of the formula VIII

(VIII)

with a strong base, and reacting the resulting aryl acetylide with an acylating agent of the formula XIII

(XIII)

wherein X is $C_1$–$C_6$ trihalomethyl, preferably trifluoromethyl; $C_1$–$C_6$ alkyl or an optionally substituted or di-substituted phenyl group of formula II; and Q is a leaving group, to give the compound of formula III.

In embodiments of the process wherein X is trifluoromethyl, the compound of the formula III can also be prepared by
(i) contacting an aryl acetylene of the formula VIII

(VIII)

with carbon monoxide, oxygen, and methanol, in the presence of a palladium (II) catalyst to provide a propargylic ester of the formula VI

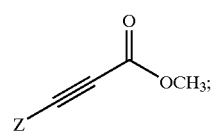

(VI)

and
(ii) treating the propargylic ester of the formula VI with trimethyl(trifluoromethyl)silane
in the presence of cesium fluoride to give the compound of formula III In another aspect, the invention relates to certain compounds, that among other things, are useful as intermediates for the preparation of the compound of the formula I. For example, the invention provides an alkyne having the formula III

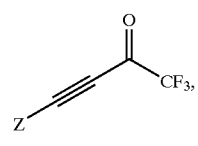

(III)

wherein Z is selected from the group consisting of substituted and unsubstituted aryl Examples of representative Z groups for the alkyne of the formula III are as discussed above for the process aspect of the invention. Preferred Z groups for the alkyne of the formula III are 3-indolyl and p-methyl.

In another aspect, the invention relates to a compound of the formula I

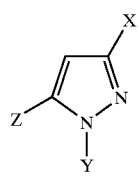

(I)

wherein X is trifluoromethyl, Y is sulfamyl, and Z is 3-indolyl or substituted 3-indolyl. In a preferred embodiment of the compound of the formula I, Z is 3-indolyl.

DETAILED DESCRIPTION OF THE INVENTION

The following terms shall have, for the purposes of this application, the respective meanings set forth below.

"aryl" alone or in combination, includes carbocylic aromatic systems or a heterocyclic aromatic systems (also known as heteroaryl). The systems may contain one, two or three rings wherein such ring may be attached together in a pendent manner or may be fused.

"inert organic solvent" means any organic solvent or combination of solvents that is unreactive in the reaction being conducted, and is a solvent for the reactants. Examples of such solvents used in the various reactions of this invention are identified in the discussion of the reaction schemes and in the examples.

"lower alkoxy" shall include linear or branched $C_1$ to $C_6$ alkoxy groups, unless otherwise specified.

"lower alkyl" alone or in combintion shall include linear or branched $C_1$ to $C_6$ alkyl groups, unless otherwise specified.

"strong base" means a non aqueous base such as sodium-, potassium-, lithium hexamethyldisilazide, lithium diisopropyl amide, and the like.

In accordance with the present invention, novel processes and synthetic intermediates for the preparation of 1,5-diaryl-3-substituted-pyrazoles are provided. The processes of the invention have been developed from readily available and inexpensive starting materials. Furthermore, the processes provide high yields of 1,5-diaryl-3-substituted-pyrazoles, and simplify isolation and purification steps.

Scheme 1

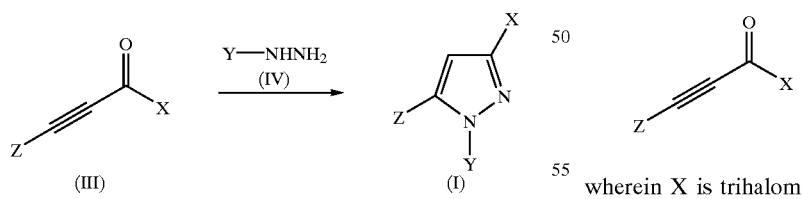

One embodiment of the invention is depicted in Scheme 1, wherein X, Y and Z are as described above for the compound of formula I. An aryl alkyne of the formula III, is condensed with an aryl hydrazine of the formula IV to provide a 1,5-diaryl-3-substituted-pyrazole compound having the formula I. Preferably, the aryl hydrazine of the formula IV is provided as a salt, e.g., a hydrochloride salt. The reaction can be completed in a protic solvent such as ethanol, n-propanol, isopropanol, butanol or acetic acid at an elevated temperature, e.g., ethanol at reflux. Typically, a slight excess of the aryl hydrazine is used, such as from about 1.05 to about 1.3 molar equivalents. The reaction provides high regioselectivity with respect to the ratio of products obtained of the 1,5-diaryl type (i.e., compound of the formula I) to the 1,3-diaryl type (not shown). Typically, the ratio of the desired 1,5-diaryl pyrazole to the undesired 1,3-isomer is greater than 9 to 1. Purification of the compound of formula I can be conveniently carried out by recrystallization from alcohol solvents, e.g., ethanol.

Various acid addition salts of the compound of the formula I can be prepared by treatment with an organic or inorganic acid. Preferably, the acid addition salts formed are pharmaceutically acceptable salts, such as those described in U.S. Pat. No. 5,563,165, the disclosure of which is herein incorporated by reference. Suitable base addition salts of the compound of formula I, wherein the phenyl group at the 5-position of the pyrazole ring incorporates a carboxy or hydroxyl substituent. Base addition salts include metallic addition salts, e.g, sodium, potassium, and organic base addition salts, e.g, organic amines. Other pharmaceutically acceptable acid addition salts are detailed in U.S. Pat. No. 5,563,165.

The aryl hydrazine compound of the formula IV can be prepared by treating substituted aryl amines of the formula XI $$Z-NH_2 \qquad (XI)$$

with nitrous acid (e.g., formed from hydrochloric acid and sodium nitrite) to provide a diazonium salt. Typically the reaction is carried out as an aqueous mixture at temperatures below about 5° C. The resulting diazonium salt is treated with a reducing agent, e.g., stannous chloride, to provide the substituted aryl hydrazine of the formula IV It will be appreciated by those of ordinary skill in the art that alternative well-known preparations of aryl hydrazine compounds can also be used, for example, through nucleophilic displacement with hydrazine of aryl compounds of the formula VII

(VII)

wherein Q' is a leaving group, e.g., halides.

Preparation of the Alkyne of the Formula III (General Methods)

The alkyne of the formula III

(III)

wherein X is trihalomethyl, $C_1$–$C_6$ alkyl or a group of the formula II

(II)

can be prepared from an α,β-unsaturated ketone of the formula V

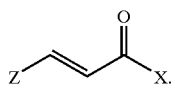 (V)

The α,β-unsaturated ketone of formula V, for example, is first treated with bromine in a suitable inert organic solvent, e.g. chloroform, at room temperature for a sufficient amount of time to form an α,β-dibromo intermediate. The intermediate is subsequently treated with a base such as an alkali metal hydroxide, e.g., potassium, sodium, or lithium hydroxide, to effect elimination of HBr and provide the alkyne of formula III. The alkyne of the formula III can be further purified by, for example, recrystallization from suitable solvents, e.g., alcohols, when the compound is a solid. Alternatively, the compound of the formula III can be purified by other techniques such as chromatography or distillation (in the case of liquids).

Scheme 2

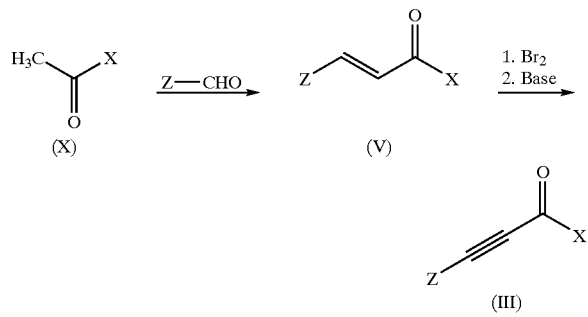

The α,β-unsaturated ketone of the formula V can be obtained by well-known aldol condensations of aryl aldehydes of the formula Z—CHO (XII) with a methyl ketone of the formula X

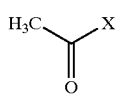 (X)

wherein X is trihalomethyl, $C_1$ to $C_6$ alkyl or a group of the formula II as depicted in Scheme 2. Typically, the reaction is carried out using a base such as an alkali metal base (e g., sodium, potassium or lithium hydroxide). The reaction can be accomplished, for example, without added solvent, or in an alcohol solvent, e.g., ethanol. The reaction can be carried out at about room temperature, although in some condensations elevated temperatures are preferably used to promote faster reaction times. After aqueous workup, the α,β-unsaturated ketones can be isolated and purified by suitable techniques such as distillation, chromatography or recrystallization.

In those embodiments wherein the methyl ketone of the formula X contains additional enolizable protons α to the carbonyl group in addition to the methyl moiety (eg., wherein the compound of the formula X is 2-pentanone) modification of the aldol reaction conditions can be used. For example, low temperature reaction conditions using a strong base, e.g, lithium diisopropylamide, in an inert organic solvent, e.g., tetrahydrofuran, can be used to generate the corresponding kinetic enolate of the methyl ketone of the formula X, which is then reacted with the aldehyde of the formula XII. Other techniques for promoting the regioselectivity of the aldol reaction will be apparent to those of ordinary skill in the art.

In another embodiment, the propargylic ester of the formula III, can be obtained by formation of the corresponding aryl acetylide from the aryl alkyne having the formula VIII

 (VIII)

with a strong base, e.g., n-butyllithium, lithium diisopropylamide, followed by addition of the acetylide to an acylating agent having the formula XIII

 (XIII)

wherein X is as defined above and Q is a leaving group. Examples of acylating agents include anhydrides, acid chlorides, activated esters and the like. The reaction is typically carried out in an ether solvent, e.g., tetrahydrofuran, methyl t-butyl ether or in dichloromethane or dimethylformamide.

Processes for the Preparation of the Alkyne of the Formula III wherein the Radical X is Trihalomethyl In addition to the general procedures described above for the alkyne of formula III, there are alternative procedures that are useful in instances where the radical X is trihalomethyl in the alkyne of formula III. For example, the alkyne of formula III wherein the radical X is trihalomethyl, can be prepared from the α,β-unsaturated ketone of the formula V

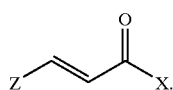 (V)

The α,β-unsaturated ketone of the formula V wherein the radical X is trihalomethyl, can be prepared from a dialkyl methylphosphonate, an N-phenyltrihaloacetamidoyl chloride and an aryl aldehyde of the formula Z—CHO (XII). An intermediate is formed from the reaction of dialkyl methylphosphonate, N-phenyltrihaloacetamidoyl chloride and a strong base (e.g., lithium diisopropylamide) that is condensed with the aryl aldehyde of the formula XII to form the α,β-unsaturated ketone of the formula V. The bromination/elimination procedure described above can then be used to convert the α,β,-unsaturated ketone of the formula V to the alkyne of the formula III.

Preparation of the Alkyne of the Formula III wherein X is Trifluoromethyl

In addition to preparations described above for the general preparation of the alkyne of the formula III and the preparations wherein the radical X is trihalomethyl, there are specific processes that are useful for the preparation of the alkyne of the formula III, where the radical X is trifluoromethyl. Some of these processes are depicted in Schemes 3–5, and are also described below.

Scheme 3

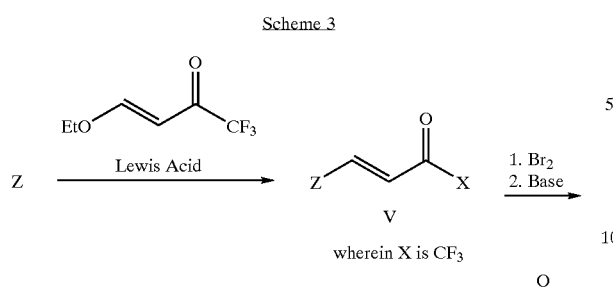

wherein X is CF₃

In some embodiments of the process, wherein the radical X is trifluoromethyl, the alkyne of the formula III is obtained from the α,β-unsaturated ketone of the formula V using the bromination/elimination procedure described above. The α,β-unsaturated ketone of the formula V is obtained by electrophilic addition of the vinylogous ester, 4-ethoxy-1,1,1-trifluoro-3-buten-2-one, to an aryl compound of the formula Z, wherein Z is as defined above (Scheme 3). For example, toluene can be treated with an equimolar amount of 4-ethoxy-1,1,1-trifluoro-3-buten-2-one in a suitable inert solvent, e.g., dichloromethane, to provide 1,1,1-trifluoro-4-(4-methylphenyl)-3-buten-2-one Typically, a catalytic amount, e.g., <10 mole %, of a Lewis acid, e.g., zinc chloride, is added to the reaction mixture to catalyze the addition.

Scheme 4

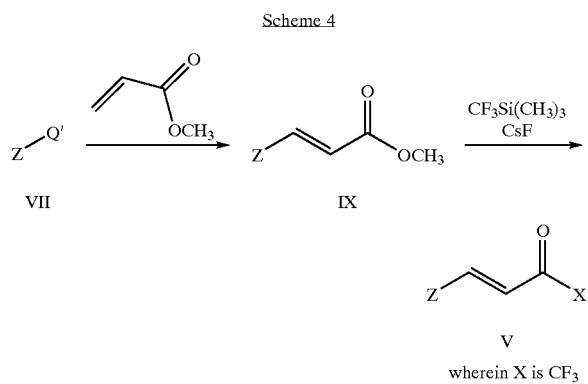

wherein X is CF₃

In other embodiments of the process, wherein the radical X is trifluoromethyl, the α,β,-unsaturated ketone of the formula V is obtained by treatment of an α,β-unsaturated ester of the formula IX with trimethyl(1,1,1-trifluoromethyl)silane and cesium fluoride (Scheme 4). The reaction is carried out neat, or in an inert organic solvent, e.g, dichloromethane, tetrahydrofuran, at a temperature of about 15 to about 30° C. The α,β-unsaturated acid ester of the formula IX can be obtained from a Heck coupling of a haloaryl compound of the formula VII (wherein Q' is a leaving group, preferably Cl, Br, or I, more preferably Br or I) with methyl acrylate. The reaction mixture includes a base, e.g., potassium carbonate, and a palladium catalyst. Palladium catalysts for the Heck reaction are well-known and include palladium(II) acetate. A stabilizing ligand for the palladium such as triphenylphosphine can be included in the reaction mixture. A preferred catalyst is Pd—Cu-Mont. K-10 (clay). The reaction is typically carried out in a dipolar aprotic solvent, e.g., dimethylformamide, at temperatures of about 100 to about 160° C. The Heck procedure permits regioselective coupling of the methyl acrylate group on to the aryl ring. This procedure is particularly advantageous for compounds wherein the electrophilic addition of the vinylogous ester to the aryl precursors Z described above leads to unfavorable mixtures of regioisomers in the product.

Scheme 5

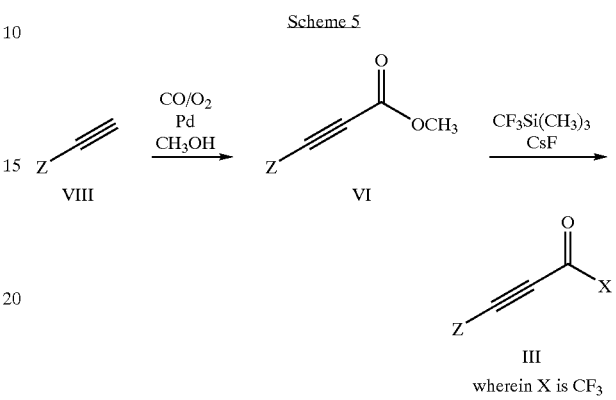

wherein X is CF₃

In another embodiment of the process, the alkyne of the formula III, wherein the radical X is trifluoromethyl is obtained by treatment of a propargylic ester of the formula VI, with trimethyl(1,1,1-trifluoromethyl)silane and cesium fluoride (Scheme 5). Here again, the reaction is carried out neat, or in an inert organic solvent, e.g, dichloromethane, tetrahydrofuran, at a temperature of about 15 to about 30° C.

The propargylic ester of the formula VI can be obtained from an aryl acetylene having the formula VIII. The reaction is catalyzed by a palladium (II) catalyst, e.g., palladium (II) acetate, in methanol at a temperature of about 15° C. to about 40° C. Preferably, the reaction catalyzed by a catalyst mixture having palladium (II) (e.g., palladium (II) acetate), molybdovanadophosphate (NPMoV), and chlorohydroquinone (HQ-Cl).

In embodiments of the processes wherein the aryl groups Y and Z, or a group of the formula II

bear substituents such as hydroxyl or carboxy that may interfere or decrease the yield of certain synthetic steps, suitable protecting groups for these substituents that are well known in the art, can be used. The protecting groups can be then removed at appropriate points in the synthetic sequence by known methods. Thus, for example, a hydroxyl moiety can be protected as a methyl or silyl ether. Similarly, a carboxy moiety can be protected as an ester if necessary, which can be hydrolyzed in a later synthetic step.

The following examples further illustrate the present invention, but of course, should not be construed as in any way limiting its scope.

EXAMPLE 1

Synthesis of 4-[5-(4-methylphenyl)-3-(trifluoromethyl)-1H-pyrazol-1-yl]benzenesulfonamide (Compound of the Formula I, X=$CF_3$, Y=sulfamyl, Z=p-methylphenyl).

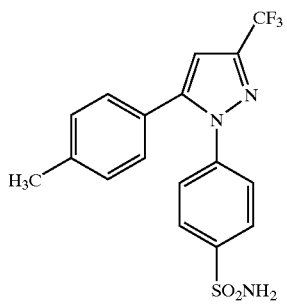

Preparation of 1,1,1-Trifluoro-4-(4-methylphenyl)-3-buten-2-one (α,β,-Unsaturated Ketone of the Formula V, X=$CF_3$):

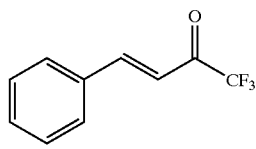

To a solution of toluene (10 mmol) and 4-ethoxy-1,1,1-trifluoro-3-buten-2-one (10 mmol) in dichloromethane (10 mL) is added zinc chloride (0.015 g, 1.5 mol %) The reaction mixture is stirred for 3 h at 22° C. The resulting precipitate is filtered, washed with dichloromethane (2×15 mL) and dried.

Preparation of 1,1,1-Trifluoro-4-(4-methylphenyl)-3-butyn-2-one (Aryl Alkyne of the Formula III, X=$CF_3$, Z=4-methylphenyl):

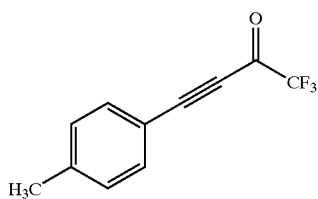

To a stirred solution of 1,1,1-trifluoro-4-(4-methylphenyl)-3-buten-2-one (10 mmol) in chloroform (100 mL), a solution of bromine (10 mmol) in chloroform (50 mL) is added dropwise at room temperature. The solution is stirred for an additional 30 min to complete of the reaction. The solvent is then removed under vacuum to obtain the dibromo compound.

The dibromo compound is added in portions to a solution of ethanolic (200 mL) potassium hydroxide (10 mmol) over a period of 30 min. After the addition is complete, the reaction mixture is refluxed for 3 h, cooled and poured onto ice cold water. The precipitated 1,1,1-trifluoro-4-(methylphenyl)-3-butyn-2-one is separated by filtration and recrystallized.

Preparation of 4-Sulfamylphenyl Hydrazine Hydrochloride (Aryl Hydrazine of the Formula IV, Y=4-sulfamyl):

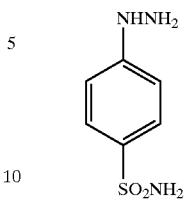

(A procedure is described in *J. Med Chem.* 1979, 22, 321–325.) A cold stirred mixture of sulfanilamide (34.2 g, 0.2 mol), hydrochloric acid (100 mL) and crushed ice (200 g) is diazotized by dropwise addition of sodium nitrite (14 g, 0.2 mol) in water (25 mL) over 30 min. The cold diazonium salt thus formed is rapidly added to a well-cooled solution of stannous chloride (100 g) in hydrochloric acid (150 mL) with vigorous stirring, and the resulting mixture is left in the refrigerator overnight. The precipitated 4-sulfamylphenyl hydrazine hydrochloride is collected at pump and dried.

Preparation of 4-[5-(4-methylphenyl)-3-(trifluoromethyl)-1H-pyrazol-1-yl]benzenesulfonamide (Compound of the Formula I)

A solution of 1,1,1-trifluoro-4-(methylphenyl)-3-butyn-2-one (10 mmol) in ethanol (100 mL) is refluxed with 4-sulfamylphenyl hydrazine hydrochloride (12 mmol) for 4 h. The reaction mixture is cooled and diluted with water. The precipitated crude 4-[5-(4-methylphenyl)-3-(trifluoromethyl)-1H-pyrazol-1-yl]benzenesulfonamide is filtered and recrystallized.

EXAMPLE 2

Preparation of 4-(5-Phenyl-3-methyl-1H-pyrazol-1-yl)benzenesulfonamide (Compound of the Formula I, X=$CH_3$, Y=4-sulfamyl, Z=phenyl)

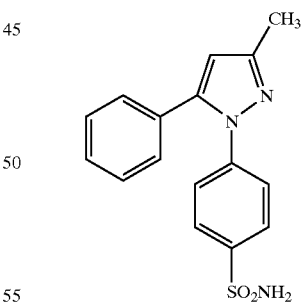

A solution of 4-phenyl-3-butyn-2-one (10 mmol) in ethanol (100 mL) was refluxed with 4-sulfamylphenyl hydrazine hydrochloride (12 mmol) for 4 h. The reaction mixture was cooled and diluted with water. The precipitated crude 4-(5-phenyl-3-methyl-1H-pyrazol-1-yl)benzenesulfonamide was filtered and recrystallized from ethanol to provide the purified product: m.p. 212–213° C. (74% yield). $^1$H NMR (DMSO-$d_6$) δ 2.3 (2, 3H), 6.2 (s, 2H), 6.5 (s, 1H), 7.2–7.3 (m, 2H), 7.38–7.48 (m, 4H), 7.75–7.82 (d, 2H).

EXAMPLE 3

Preparation of 1,1,1-Trifluoro-4-Phenyl-3-Butyn-2-one (Compound of the Formula III, Z=phenyl, X=CF₃)

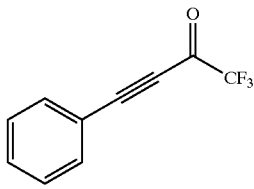

Preparation of Methyl Phenylpropiolate (Propargylic Ester of the Formula VI, Z=Phenyl)

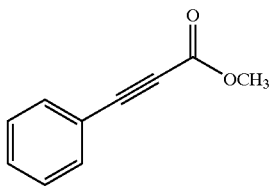

A solution of phenylacetylene (2 mmol), chlorohydroquinone(HQ-Cl) (0.4 mmol), molybdovanadophosphate (NPMoV) (35 mg) and palladium (II) acetate (50 mg) in methanol (10 mL) is stirred under $CO/O_2$ (10 atm/0.5 atm) at 25° C. for 15 h. The reaction is then quenched with wet ether and the product is extracted with n-hexane. After removal of the solvent under reduced pressure, the product is isolated by column chromatography over silica gel (hexane ethyl acetate 5:1) to give pure methyl phenylpropiolate.

Conversion of Methyl Phenylpropiolate to 1,1,1-Trifluoro-4-Phenyl-3-Butyn-2-one (Alkyne of the Formula III, Z=Phenyl, X is CF₃)

At room temperature, CsF (0.15 g, 1 mmol) is added to a mixture of methyl phenylpropiolate (1.62 g, 10 mmol) and TMS-CF₃ (1.46 g, 10.25 mol, Lancaster). After completion of the reaction (3 h), hydrolysis is carried over 3 h by using 4 N HCl (4 mL). The resulting product is extracted with ether (30 mL). After removing the ether, the trifluoromethylated ketone is obtained.

EXAMPLE 4

Synthesis of trans-1,1,1-trifluoro-4-aryl-3-buten-2-one (α,β-Unsaturated Ketone of formula V (X=CF₃)

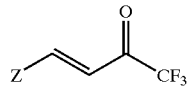

To a solution of 10% sodium hydroxide in ethanol (25 mL), 1,1,1-trifluoroacetone (10 mmol) is added and stirred at 15–20° C. To this a solution of the appropriate aryl aldehyde (10 mmol)

$$Z—CHO \quad (XII)$$

where Z is defined as above, is added and stirred vigorously for 4 hrs. The temperature of the reaction is maintained at 15–20° C. throughout the reaction. The solution is then poured into ice water and acidified with concentrated hydrochloric acid. The resulting separated trans-1,1,1-trifluoro-4-aryl-3-buten-2-one of formula V (X=CF₃) is extracted with ether and dried over anhydrous MgSO₄. Evaporation of the dried ethereal layer yields the trans-1,1,1-trifluoro-4-aryl-3-buten-2-one which is purified by recrystallization.

The appropriate 1,1,1-trihaloacetone can be substituted for 1,1,1-trifluoroacetone in this procedure to provide other trans-1,1,1-trihalo-4-aryl-3-buten-2-one intermediate.

Alternative Synthesis of trans-1,1,1-trifluoro-4-aryl-3-buten-2-one intermediate (X=CF₃)

To a cooled solution of (−70° C.) lithium diisopropylamide (10 mmol), diethyl methylphosphonate (5 mmol) is added. After the mixture is stirred for 30 minutes at −70° C., N-phenyltrifluoroacetimidoyl chloride (5 mmol) is gradually added and stirring is continued at −70° C. for 1 hour. The appropriate araldehyde (5 mmol)

$$Z—CHO \quad (XII)$$

where Z is defined as above is added dropwise for 10 minutes. The resulting mixture is warmed to room temperature over 2 hours and then stirred overnight. Then 20 mL of dilute hydrochloric acid is added and stirred at room temperature for 4 hours. The solution is extracted thrice with diethyl ether (20 mL each time) and washed successively with 5% sodium bicarbonate and brine until the pH of the solution is 6. The ethereal layer is separated, dried over anhydrous sodium sulfate and concentrated under reduced pressure to yield crude trans-1,1,1-trifluoromethyl-4-aryl-3-buten-2-one. The product is purified either by column chromatography or by recrystallization.

Similarly, other N-phenyltrihaloacetimidoyl chlorides can be substituted for N-phenyltrifluoroacetimidoyl chloride in this procedure to produce other trans-1,1,1-trihalo-4-aryl-3-buten-2-one intermediates.

EXAMPLE 5

Synthesis of trans-1-(alkyl or optionally substituted aryl)-3-aryl-2-propen-1-one intermediate

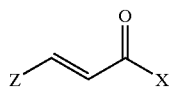

To a solution of 10% sodium hydroxide in ethanol (25 mL), a ketone of the formula

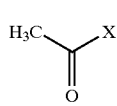

wherein X is $C_1$–$C_6$ alkyl (20 mmol), or a radical of formula II

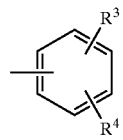

wherein $R_3$ and $R_4$ are defined as above (10 mmol), is added and stirred at 15–20° C. To this a solution of the appropriate aryl aldehyde

Z—CHO (XII)

(10 mmol) where Z is defined as above, is added and stirred vigorously for 4 hours. The temperature of the reaction is maintained at 15–20° C. throughout the reaction. The solution is then poured into ice water and acidified with concentrated hydrochloric acid The resulting separated trans-1-(alkyl or optionally substituted aryl)-3-aryl-2-propen-1-one of formula V (X=$C_1$–$C_6$ alkyl, or radical of formula II) is extracted with ether dried over anhydrous $MgSO_4$. Evaporation of the dried ethereal layer yields the trans-1-(alkyl or optionally substituted aryl)-3-aryl-2-propen-1-one, which is purified by distillation or recrystallization.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A process for preparing a compound of the formula I

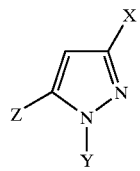

(I)

wherein

X is selected from the group consisting of trihalomethyl, $C_1$–$C_6$ alkyl, and a group of the formula II

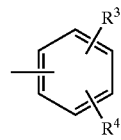

(II)

wherein $R^3$ and $R^4$ are independently selected from the group consisting of hydrogen, halogen, hydroxyl, nitro, $C_1$–$C_6$ alkyl, $C_1$–$C_6$ alkoxy, carboxy, $C_1$–$C_6$ trihaloalkyl, cyano, alkylsulfonyl, sulfamyl, phosphonato, and hydroxyalkyl;

Y is p-sulfamylphenyl; and

Z is selected from the group consisting of substituted and unsubstituted aryl; the process comprising: condensing an alkyne of formula III

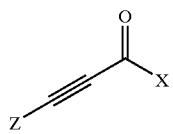

(III)

with an aryl hydrazins of the formula Y—$NHNH_2$ (IV) or a salt thereof.

2. The process of claim 1, wherein Z is substituted or unsubstituted heteroaryl.

3. The process of claim 2, wherein Z is selected from the group consisting of substituted and substituted indolyl, furyl, thienyl, pyridyl, benzofuryl, benzothienyl, imidazolyl, pyrazolyl, thiazolyl, benzothiazolyl, quinolinyl, and 4-(2-benzyloxazolyl).

4. The process of claim 3, wherein Z is 3-indolyl.

5. The process of claim 1, wherein Z is selected from the group consisting of unsubstituted phenyl, mono-, di-, and trisubstituted phenyl.

6. The process of claim 5, wherein Z is phenyl substituted with one or more of halogen, hydroxyl, nitro, $C_1$–$C_6$ alkyl, $C_1$–$C_6$ alkoxy, carboxy, $C_1$–$C_6$ trihaloalkyl and cyano.

7. The process of claim 1, wherein X is trifluoromethyl.

8. The process of claim 1, wherein X is sciected from the group consisting of $C_1$–$C_6$ alkyl and a group of thc fomula II wherein $R^3$ and $R^4$ are independently selccted from the group consisting of halogen, hydroxyl, nitro, $C_1$–$C_6$alkyl, $C_1$–$C_6$alkoxy, carboxy, $C_1$–$C_6$ trihaloalkyl, cyano, alkylsulfonyl, sulfamyl, phosphonato, and hydroxyalkyl.

9. The process of claim 1, wherein X is trifluoromethyl, Y is 4-sulfamyl and Z is substituted phenyl.

* * * * *